United States Patent
Kaimori et al.

(10) Patent No.: US 8,282,813 B2
(45) Date of Patent: Oct. 9, 2012

(54) BIOSENSOR MEASUREMENT MACHINE, BIOSENSOR MEASUREMENT SYSTEM AND BIOSENSOR MEASUREMENT METHOD

(75) Inventors: Shingo Kaimori, Osaka (JP); Toshifumi Hosoya, Osaka (JP); Moriyasu Ichino, Osaka (JP); Takahiko Kitamura, Osaka (JP); Isao Karube, Ibaraki (JP); Masao Gotoh, Ibaraki (JP); Hideaki Nakamura, Ibaraki (JP); Tomoko Ishikawa, Ibaraki (JP)

(73) Assignees: Sumitomo Electric Industries, Ltd., Osaka (JP); National Institute of Advanced Industrial Science and Technology, Tokyo (JP)

( * ) Notice: Subject to any disclaimer, the term of this patent is extended or adjusted under 35 U.S.C. 154(b) by 831 days.

(21) Appl. No.: 11/992,102

(22) PCT Filed: Sep. 8, 2006

(86) PCT No.: PCT/JP2006/317897
§ 371 (c)(1),
(2), (4) Date: Mar. 14, 2008

(87) PCT Pub. No.: WO2007/032286
PCT Pub. Date: Mar. 22, 2007

(65) Prior Publication Data
US 2009/0152127 A1    Jun. 18, 2009

(30) Foreign Application Priority Data

Sep. 14, 2005  (JP) ................................. 2005-267706

(51) Int. Cl.
*G01N 27/416* (2006.01)
(52) U.S. Cl. .... 205/792; 204/401; 204/406; 204/403.02
(58) Field of Classification Search .................. 204/403.01–403.15; 205/777.5, 205/778, 792; 600/345–348; 435/4–40.52; 422/68.1–98; 436/62–71, 500–548
See application file for complete search history.

(56) References Cited

U.S. PATENT DOCUMENTS

| | | | |
|---|---|---|---|
| 5,352,351 A | 10/1994 | White et al. | |
| 2003/0036054 A1* | 2/2003 | Ladisch et al. | 435/5 |
| 2003/0159945 A1* | 8/2003 | Miyazaki et al. | 205/777.5 |
| 2004/0216516 A1* | 11/2004 | Sato | 73/64.56 |
| 2006/0224658 A1* | 10/2006 | Sato et al. | 708/801 |

FOREIGN PATENT DOCUMENTS

| | | |
|---|---|---|
| EP | 1 369 684 A1 | 12/2003 |
| EP | 1 443 322 A1 | 8/2004 |
| JP | 8-15220 | 1/1996 |
| JP | 9-274010 | 10/1997 |
| WO | WO 03/012421 A1 | 2/2003 |
| WO | WO 2004/011921 A1 | 2/2004 |

* cited by examiner

*Primary Examiner* — Kaj K Olsen
*Assistant Examiner* — Susan D Leong
(74) *Attorney, Agent, or Firm* — McDermott Will & Emery LLP

(57) ABSTRACT

A biosensor measurement device for providing accurate measurement results within a short period of time by using only a very small amount of sample. The biosensor measurement device includes a power source, which is connected to a voltage regulator, a measurement instrument, and a controller for supplying power. When the biosensor chip is connected to the biosensor measurement device and a voltage is applied, the measurement instrument begins the measurement of a current value for the biosensor. When the measured current value or a measured charge value is greater than a reference value, the measurement is terminated in accordance with an instruction issued by the controller, and when the value is smaller than the reference value, the measurement is continued in accordance with a controller instruction.

6 Claims, 9 Drawing Sheets

PRIOR ART

PRIOR ART

BIOSENSOR MEASUREMENT MACHINE, BIOSENSOR MEASUREMENT SYSTEM AND BIOSENSOR MEASUREMENT METHOD

RELATED APPLICATIONS

This application is the U.S. National Phase under 35 U.S.C. §371 of International Application No. PCT/JP2006/317897, filed on Sep. 8, 2006, which in turn claims the benefit of Japanese Application No. 2005-267706, filed on Nov. 14, 2005, the disclosures of which Applications are incorporated by reference herein.

TECHNICAL FIELD

The present invention relates to a biosensor measurement machine that employs a biosensor chip to measure chemical substances, and a biosensor measurement system and a biosensor measurement method.

BACKGROUND ART

To perform a measurement by employing a biosensor chip, a sample to be measured is introduced in the reaction portion of a biosensor, a biochemical reaction, such as an enzymatic reaction or an antigen-antibody reaction, is generated in the reaction portion, and information obtained through this biochemical reaction is output, by the biosensor chip, to a measurement apparatus that analyzes the sample. A measurement method employing a biosensor chip is performed by employing a superior molecular recognition function possessed by an organism, and has drawn attention as a method for enabling the performance of a quick and simple measurement of a chemical substance by employing only a tiny amount of a sample. As an example, the measurement method using a biosensor chip can be employed to measure the glucose content of blood (blood sugar level) or a urine sugar level, and can be used, for example, for a home health examination (self-care) for the self-control and management of diabetes.

A measurement method using a biosensor chip described in patent document 1 is known. According to this biosensor measurement method, as shown in FIG. 8, a biosensor 100 includes two leads 101 and 102, and the distal ends of the leads 101 and 102 are to be connected to two terminals 104 and 105 of a connector 103. When the biosensor 100 is connected to the connector 103, a voltage is applied using a battery 106, the resistances of electrodes are changed by a sample present in the biosensor 100, and the system function is initiated. Then, a microcomputer 107 detects, through an A/D converter 109, a change in a voltage output by a current/voltage converter 108, and starts a measurement timer. At the same time, a switch 110 is closed, and the two electrodes of the biosensor 100 are short-circuited, so that the two electrodes can be set to equal potential states, i.e., to states near a potential difference of 0 V. As a result, a potential difference that occurred between the two electrodes can be easily removed.

As another example, a measurement method employing a biosensor chip described in patent document 2 is known. According to this measurement method for employing a biosensor, as shown in FIG. 9, a biosensor 200 and a connector 201 are connected by resistors 202 and 203 arranged between the individual leads of the two electrodes and the individual terminals of the connector 201. And a GDO enzyme, a potassium ferricyanide electron acceptor, a phosphate buffer solution and a glucose substrate are introduced in the electrode system and a current flowing through the electrode system is measured. The current is detected by a detection circuit 204, and is converted into a voltage signal by a current/voltage converter 205. The thus obtained voltage signal is converted into a digital signal by an A/D converter 206, the digital signal is processed by a CPU 207 and a resultant signal is output to an LCD display device 208 and can also be recorded in a memory 209.

Patent Document 1: Japanese Patent Application Laid-Open: JP-A-8-15220

Patent Document 2: Japanese Patent Application Laid-Open: JP-A-9-274010

DISCLOSURE OF THE INVENTION

Problems to be solved by the Invention

In a conventional case of the use of a biosensor chip for measuring a sample, almost the same period of time is required for any measurement, regardless of whether the concentration of a measurement sample is high or low. Further, a long measurement period, e.g., several tens of seconds, is required in order to obtain precise measurement results. However, depending on the concentration of a measurement sample, precise results can be obtained within a short measurement period, and a reduction in the length of the measurement period has been requested. Furthermore, demands for measurements performed using biosensor chips have increased, and in accordance with the increase in the measurements demands, multiple measurement samples must be handled within a short period of time. One objective of the present invention is to provide a biosensor measurement machine, and a measurement method therefor, whereby a measurement can be ended within a short period of time and accurate measurement results can be obtained.

Means for Solving the Problems

According to the present invention, there is provided a biosensor measurement machine including:

a voltage application unit for applying a voltage to a biosensor chip;

a measurement unit for measuring a current or a charge generated by the voltage application unit; and a control unit for determining whether a measurement should be continued, based on a current value or a charge value measured by the measurement unit.

Further, according to the present invention, preferably, there is provided the biosensor measurement machine, wherein the control unit compares the current value or the charge value with a reference value therefor to determine whether the measurement should be continued, and a plurality of different values are prepared for use as reference values. The comparison of the current value or the charge value with a reference value includes a case wherein a calculation process is performed for a current value or a charge value, and the obtained value is employed for a comparison.

In addition, according to the present invention, preferably, there is provided the biosensor measurement machine, wherein the control unit also includes a plurality of different standard curve tables.

According to the present invention, there is provided a biosensor measurement system including:

a biosensor measurement machine as described above, and a biosensor chip.

Moreover, according to the present invention, preferably, there is provided the biosensor measurement system, wherein a biosensor chip includes glucose oxidase as an enzyme, and has a cavity volume equal to or smaller than 300 nl (nanoliters).

According to the present invention, there is provided a biosensor measurement method including the steps of:

applying a voltage to a biosensor chip;

measuring a current or a charge generated by application of the voltage; and determining whether a measurement should be continued, based on a current value or a measured charge value.

Effects of the Invention

According to the biosensor measurement machine and the measurement method of the present invention, since whether a measurement is to be continued is determined based on a current value or a charge value that has been measured, the measurement can be terminated within a short period of time and accurate measurement results can be obtained.

DESCRIPTION OF REFERENCE NUMERALS AND SIGNS

Figure 1:
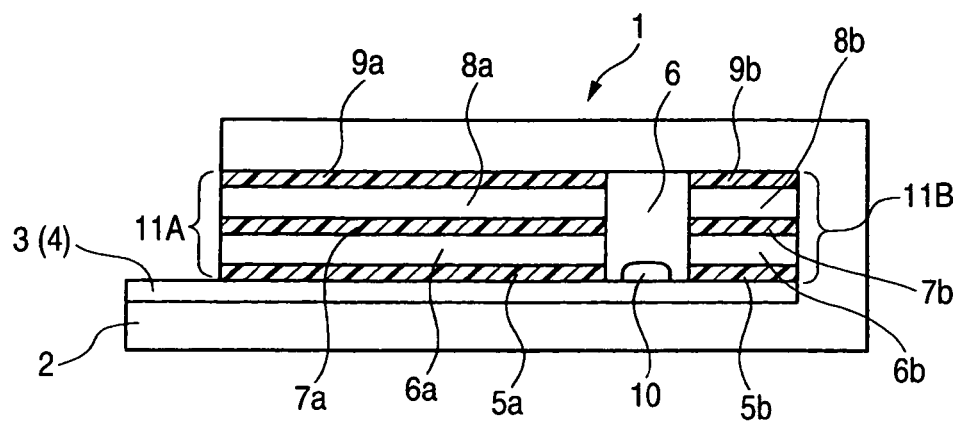
FIG. 1 shows an overview of a biosensor chip, with FIG. 1(*a*) being an explanatory view, taken from a side face, and FIG. 1(*b*) being an explanatory view, taken from a top face.
Figure 1:
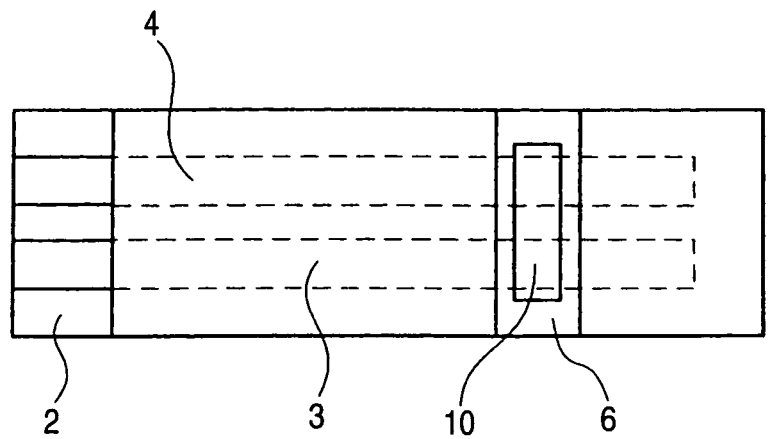

1: biosensor chip
2: substrate
3, 4: electrode
6: reaction space
10: drug
11A, 11B: sheet member
20: biosensor measurement machine
21: power source
22: voltage regulator
23: measurement instrument
24: controller
25: display device

BEST MODE FOR CARRYING OUT THE INVENTION

A biosensor measurement machine, a biosensor measurement system and a biosensor measurement method according to the present invention will be described in detail below, while referring to drawings.

First, the overview of a biosensor will be described. An example in FIG. 1 shows the main arrangement of a biosensor chip: FIG. 1(*a*) is an explanatory view, taken from the side face, and FIG. 1(*b*) is an explanatory view, taken from the top face. A biosensor chip 1 includes a substrate 2 that is folded into almost a U shape in cross section, and on one of the surfaces of the substrate 2, two electrodes 3 and 4 and their lead lines are formed, substantially parallel to each other, using screen printing. On the upper faces of the electrodes 3 and 4 and on the portion of the substrate 2 on which the electrodes 3 and 4 are not screen-printed, two adhesive layers 5*a* and 5*b* are deposited longitudinally (from the left to the right in the drawing), except for the distal end side (at the left in the drawing) and a portion that becomes a hollow reaction space 6. First spacer members 6*a* and 6*b* are arranged on the surfaces of the adhesive layers 5*a* and 5*b*, and further, second spacers 8*a* and 8*b* are overlaid through adhesive layers 7*a* and 7*b*, and the second spacers 8*a* and 8*b* and the other side of the substrate 2 are bonded using adhesives 9*a* and 9*b*. The reaction space 6 is defined by the substrate 2 that is folded into a U shape, and a front sheet member 11A and a rear sheet member 11B, which are formed by laminating the adhesive layers and the spacer members. The two electrodes 3 and 4 are exposed inside the reaction space 6. In addition, a drug 10 such as a catalyst or an enzyme is applied on the electrodes 3 and 4 to generate a biochemical reaction.

Figure 2:
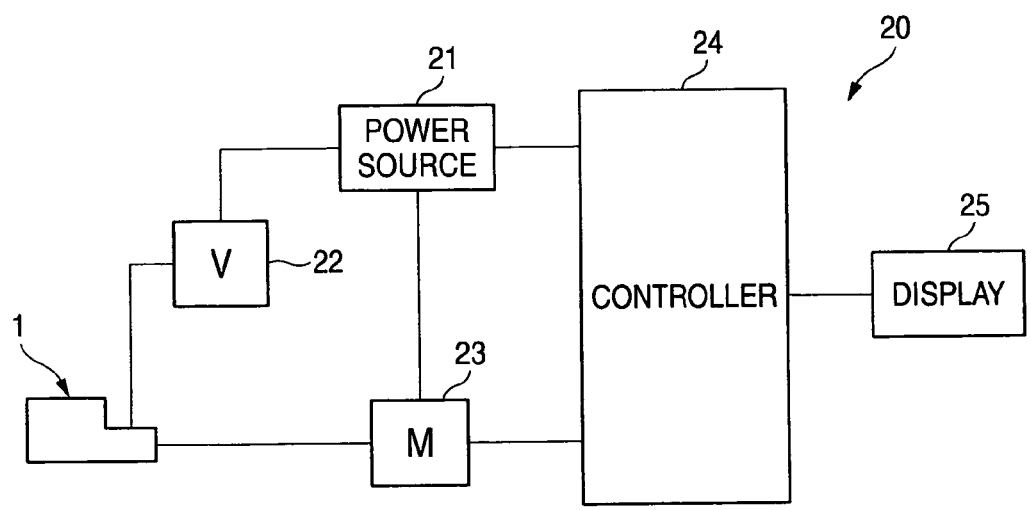
FIG. 2 is a schematic diagram for explaining a biosensor measurement machine according to the present invention.

A biosensor measurement machine according to the present invention will now be described. An overview of the biosensor measurement machine is shown in FIG. 2. This biosensor measurement machine 20 includes a power source 21, which is connected to a controller 24, a measurement instrument 23 and a voltage regulator 22 for supplying power. The voltage regulator 22 can apply a voltage to the biosensor chip 1, and through the application of a voltage to the electrodes 3 and 4 (see FIG. 1), can obtain information produced by a biochemical reaction in a sample stored in the biosensor chip 1. Further, the biosensor chip 1 is connected to the measurement instrument 23, and can obtain from the measurement instrument 23 a numerical value, or a signal, carrying information relative to a biochemical reaction in a sample. The measurement instrument 23 is connected to the controller 24 that provides a variety of control functions, and data or information measured by the measurement instrument 23 is transmitted to the controller, which then performs a computation process.

The controller 24 includes a control circuit for determining whether a data value measured by the measurement instrument 23 is greater or smaller than a predesignated value (a threshold value, a reference value, etc.), and can employ the control circuit to determine whether a measurement should be performed. Furthermore, a plurality of different reference values that are employed for a determination made for the continuation/termination of a measurement are also stored, and the continuation/termination of a measurement can be designated in accordance with the value levels. Further, a standard curve table is stored in the controller 24, and in accordance with the continuation/termination of a measurement, a desired standard curve can be selected and the measurement results produced by a biosensor chip can be computed/calculated to obtain accurate measurement results. In addition, the controller 24 is connected to a display device 25, so that the measurement results can be displayed on the display device 25, or can be stored in a storage device incorporated in the display device 25, and can, for example, be compared with measurement results obtained in the past.

A biosensor measurement system can also be arranged by employing the biosensor measurement machine of this invention and the biosensor chip shown in FIG. 1. In this case, a connector is provided for the biosensor measurement machine, and the distal end of the biosensor chip is inserted in the connector to render the two electrodes conductive, so that a sample present within the biosensor chip can be measured. The biosensor chip shown in FIG. 1 can be used only once, for a single measurement (is a so-called disposable), and a person performing a self-measurement can easily conduct the measurement at home, etc. In this case, after an organic sample is taken by the person performing the self-measurement, the sample is introduced in the reaction space of the biosensor chip, and a measurement using the measurement machine is performed by connecting the biosensor chip to the measurement machine. In this manner, the measurement results can be obtained. As described above, according to the biosensor measurement system of this invention, without a special skill being required, a person performing a self-measurement can easily prepare for and conduct a measurement, and can immediately obtain measurement results.

Figure 3:
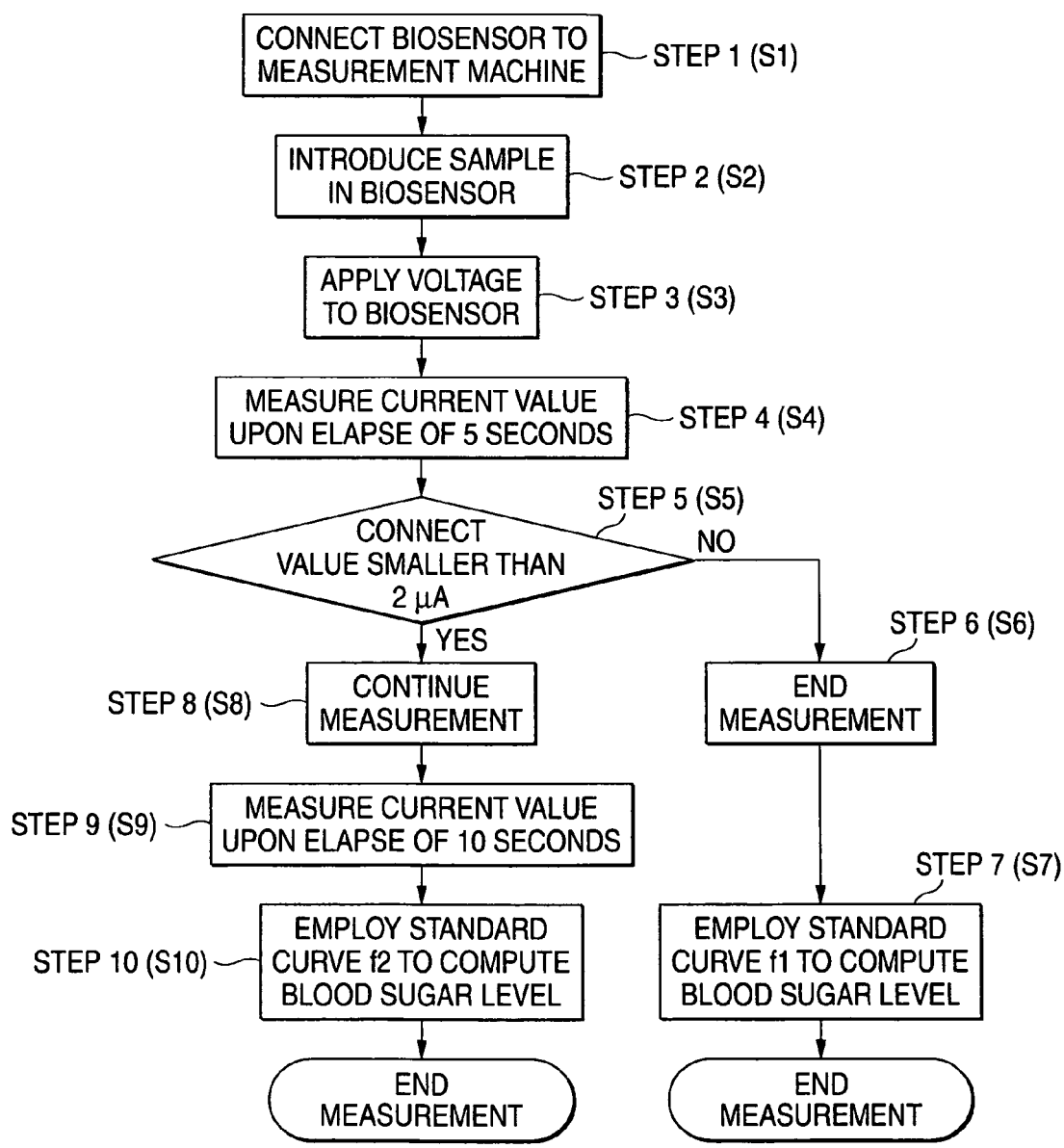
FIG. 3 is a flowchart showing an example biosensor measurement method according to the present invention.

Next, the biosensor measurement method according to the present invention will be described by being applied, for example, for a method used to measure a blood sugar level. FIG. 3 is a flowchart for explaining the process for a blood sugar level measurement method. At the first step 1 (S1), the electrode portions at the distal ends of a biosensor chip are connected to the connector of the measurement machine. When the connection to the biosensor chip is completed, at step 2 (S2), a sample is introduced in the reaction space of the biosensor chip. It is preferable that the biosensor chip shown in FIG. 1 be employed, and that the volume of the reaction space (cavity) be equal to or smaller than 300 nl (nanoliters). When the reaction space has a tiny volume equal to or smaller than 300 nl, a person performing a self-measurement need only take a little blood, and accordingly, only a short period is required to take the blood. Further, since a styptic procedure can be performed in only a short period of time, the blood taking burden for a person performing a self-measurement can be reduced. It is also preferable that glucose oxidase (GDO) be used as the enzyme that is the drug to be located in the reaction space. Since glucose oxidase has a satisfactory sensitivity characteristic and has a quick response time, an accurate measurement is enabled within a short period of time.

Figure 4:
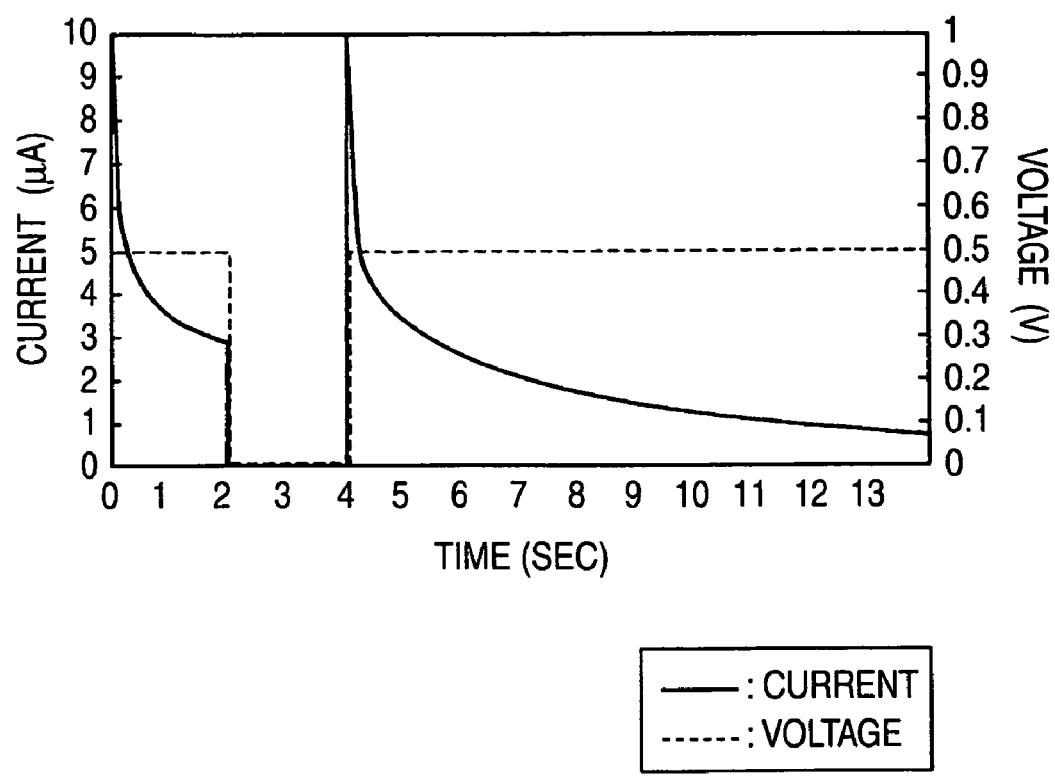
FIG. 4 is a diagram showing an example time-transient protocol for a voltage and a current that are measured.

When a sample is introduced in the reaction space of the biosensor chip in a state wherein a voltage is applied, electric conducting of the electrodes is started, so that the introduction of the sample can be detected. After step S2 has ended, a settling period of about several seconds to several tens of seconds may be designated, so that the blood sample and the enzyme contained in the drug satisfactorily react with each other in the reaction space of the biosensor chip. Following this, program control is shifted to step 3 (S3), and a voltage is applied to the biosensor chip by the voltage regulator. When the voltage is applied to the biosensor chip, the controller begins counting time, and the measurement instrument begins measurement of a current value. Examples of the thus obtained time-transient protocols for a current and a voltage are shown in FIG. 4.

Figure 5:
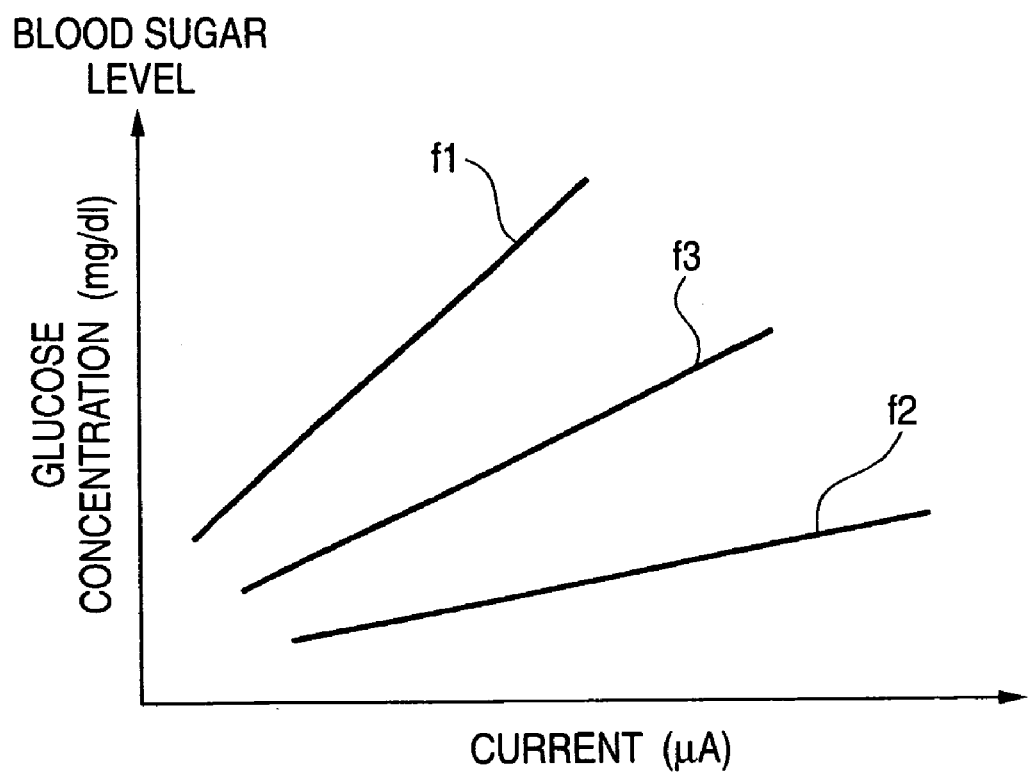
FIG. 5 is a diagram showing an example standard curve table.

When five seconds have elapsed since the start of the measurement, at step 4 (S4), the current value of the biosensor chip upon the elapse of five seconds is measured. At this time, the control circuit of the controller is started and performs a comparison to determine whether the current value is smaller or greater than a predesignated value (a reference value) that is set for the control circuit. In this mode, the predesignated setup current value (reference value) is 2 µA, and at step 5 (S5), a comparison between the measured value and the reference value is performed. When the measured value is greater than 2 µA, program control advances to step 6 (S6) and terminates measurement of the current value. Then, program control advances to step 7 (S7), and a blood sugar level is computed. Computation of the blood sugar level can be performed by employing a standard curve table stored in the controller, and an example of this standard curve table is shown in FIG. 5. In the standard curve table shown in FIG. 5, a plurality of different standard curves are provided for a relationship between a glucose concentration and a current, and in accordance with a measurement condition, a standard curve to be used for computation of a blood sugar level is determined. After program control has advanced to step 6 (S6), a standard curve f1 is employed for blood sugar level computation at step 7 (S7). The glucose concentration is obtained based on a relationship between the measured current value and the standard curve f1, and finally, a blood sugar level is obtained.

When, at step 5 (S5), the measured current value for the biosensor chip is smaller than 2 µA, program control advances to step 8 (S8), and measurement of the current value is continued. Sequentially, at step 9 (S9), a current value upon the elapse of ten seconds is measured, program control advances to step 10 (S10), and computation of a blood sugar level is performed. When the process has been shifted to step 8 (S8), the glucose concentration upon an elapse of ten seconds is obtained by employing a standard curve f2 in the standard curve table in FIG. 5, and a blood sugar level is obtained.

Figure 6:
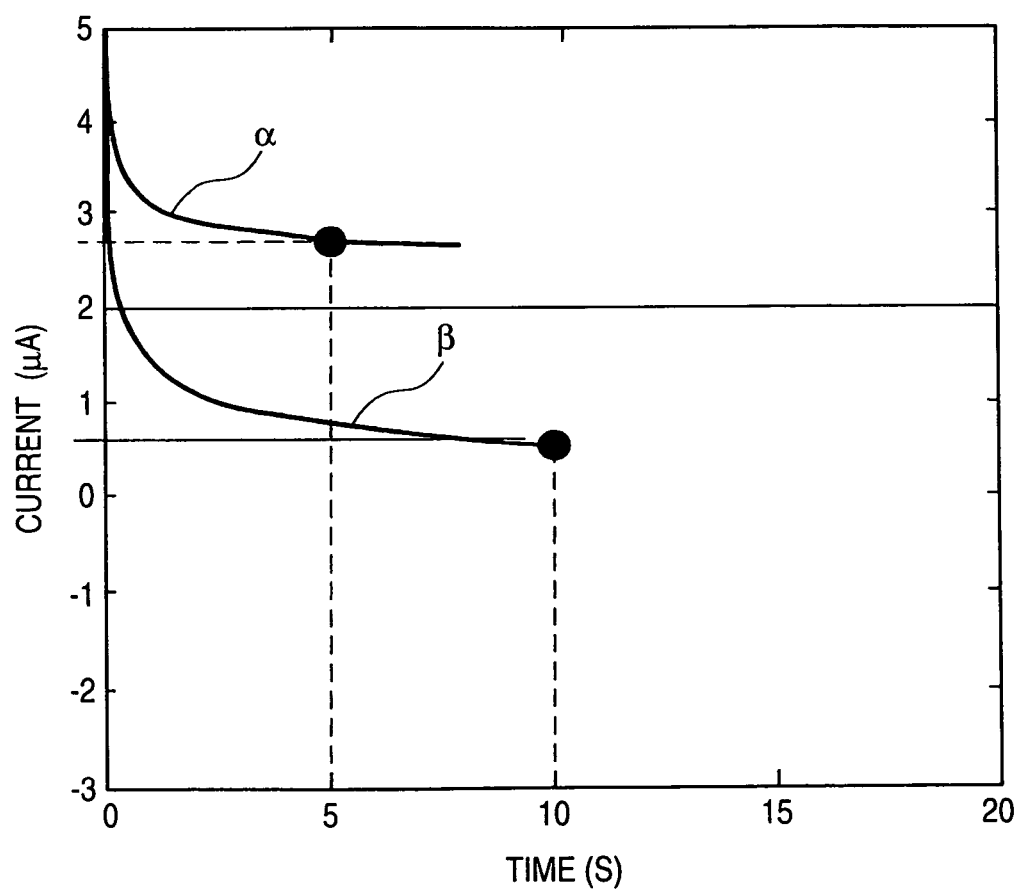
FIG. 6 is a diagram showing the elapsed time for currents measured by two biosensor chips.

The process from step 4 (S4) to step 10 (S10) will be explained based on FIG. 6. The vertical axis in this drawing represents a current value measured by the measurement instrument, and the horizontal axis represents the elapsed time from the start of a measurement. In the flowchart in FIG. 3, a biosensor chip processed through step 5, step 6 and step 7 is a first biosensor chip, and a biosensor chip processed from step 5 to step 8 through step 10 is a second biosensor chip. α indicates a current curve obtained through measurement of a sample A stored in the first biosensor chip, and β indicates a current curve obtained through the measurement of a sample B stored in the second biosensor chip. For both of the samples A and B, a trend is observed in that, immediately after the measurement is started, the current value is sharply raised to near 5 µA. The main factor for this trend is the reaction of glucose on the surfaces of the electrodes, and an impurity that is attached to the surfaces of the electrodes, and that is contained in blood, more or less affects the magnitude of the current value. After the current values of the samples A and B have been sharply raised, the reaction of glucose located separate from the electrodes is diffused and propagated to the electrodes, and accordingly, a current is supplied. However, the current value starts to be lowered in accordance with the diffusion velocity, and the inclinations of the two curves α and β begin to converge. When five seconds have elapsed, the inclination of the current curve α of the sample A becomes quite small, and the current curve starts substantially constantly in the vicinity of about 2.8 µA. Here, the current value exceeds the reference value of 2 µA, the measurement of the current value for the sample A is terminated, and the blood sugar level is computed using the standard curve f1 (see FIG. 5) that is consonant with the condition at the end of five seconds.

As described above, an impurity in the blood affects the measured value. As a factor, other than an impurity, of the time-transient fluctuation of a current value, there is a current value fluctuation that is derived from a phenomenon such that, during the introduction of a sample, air remains as bubbles on the surfaces of the electrodes, instead of being immediately removed, and the bubbles gradually escape from the surfaces of the electrodes. Further, in order to permit a drug, such as an enzyme, to react with glucose in a sample, a process for dissolving the enzyme, etc., in the sample is required. There is also a current value fluctuation that is due to the fact that much time is required for this dissolution. Either way, since these fluctuations are near zero after a predetermined period has elapsed, in accordance with the elapse of time, the measured current value converges to a value based on a glucose reaction.

As for the sample B, when five seconds have elapsed, the measured current value is about 0.8 μA, which is lower than the reference current value of 2 μA, and the measurement of the current value is continued for another five seconds. When ten seconds have elapsed from the start of the measurement, the measured current value is almost constant, i.e., 0.7 μA. The measurement is terminated at this point, and the blood sugar level for the sample B is computed using the standard curve f2 that is consonant with the condition at the end of ten seconds.

The case for the sample A is that a sample is indicated that has a high glucose concentration, i.e., has a high blood sugar level, and the sample B indicates a sample having a low glucose concentration and a low blood sugar level. Generally, since a sample having a high blood sugar level provides a high reaction level between glucose and an enzyme, a large amount of a current flows through the sample. As a result, comparatively, the sample is less affected by the reaction produced, for example, by an impurity, so that a stable measured value can be obtained even when the measurement is ended comparatively shortly after a voltage is applied. On the other hand, since a sample having a low blood sugar level provides a low reaction level between glucose and an enzyme, the absolute value of a current generated by this reaction is also small. Thus, a little period of time is required before a stable current value is obtained. Therefore, a threshold current value is predesignated, and a measurement is immediately terminated for a biosensor for a sample that exceeds the threshold value. In this manner, an accurate blood sugar value can be obtained within a short period of time.

A sample having a high blood sugar level here indicates a sample that falls within the range of a concentration equal to or higher than 30 to 50 mg/dL, in a case for a glucose sensor having a cavity volume of 1 to 5 μL. At this time, depending on the enzyme to be used and the electrode type, generally about 2 to 10 seconds is required as a period for removing the affect, for example, of an impurity. On the other hand, a sample having a low blood sugar level indicates a glucose concentration of equal to or lower than 30 to 50 mg/dL. At this time, a period of about 5 to 30 seconds is required to remove the affect, for example, of an impurity. Since the glucose concentration within this range falls outside the normal concentration range (50 to 150 mg/dL) for a human being, a frequency for measuring this concentration is low. However, since this glucose concentration is within a concentration range that is used as a determination reference to determine whether insulin should be provided for a type I diabetes mellitus patient, whether accurate measurement is available within this concentration range is important in order to extend the application range of the measurement machine. Especially in a case wherein inexpensive carbon electrodes are employed as those for a sensor, the convergence of a current value is delayed because the resistance is great, and the measurement condition is adjusted to that for a low concentration area, so that a very long measurement period must be designated. However, when the present invention is employed, in a case for a low blood sugar level, the measurement results can also be quickly displayed following a short measurement period of time within the normal concentration range, while the accuracy of the measured value is maintained.

Furthermore, recently, a small cavity volume is requested to reduce the load when a person performing a self-measurement takes blood. The cavity volume of the normal glucose sensor is about 1 to 5 μL, and when the volume is smaller than 300 nL, the absolute amount of glucose is reduced. Therefore, there is a case wherein performing a measurement in a short period of time is difficult, even within a concentration range equal to or greater than 30 to 50 mg/dL, which is included in the normal blood sugar level range for a human being. Even in this case, when the method of this invention is employed, a measurement for only the minimum required concentration range can be limited as a measurement taken during a long period of time. Therefore, while the blood taking load for a person performing a self-measurement is reduced, the loss of the measurement period can be minimized. The method of this invention is especially useful when a sensor having a small cavity volume is to be manufactured using inexpensive carbon electrodes, without drastically increasing the cost.

According to the above described mode, a blood sugar level is obtained based on a current value measured by the biosensor chip. However, instead of the measurement of a current value, the measurement of a charge may be performed to obtain an accurate blood sugar level within a short period of time. As an example, a charge value can be measured as an integral value for a current in accordance with the elapsed time indicated in the current curves α and β shown in FIG. 5. Thus, by setting a predesignated charge value (a reference charge value), whether the measurement of a sample should be ended or performed can be determined.

Figure 7:
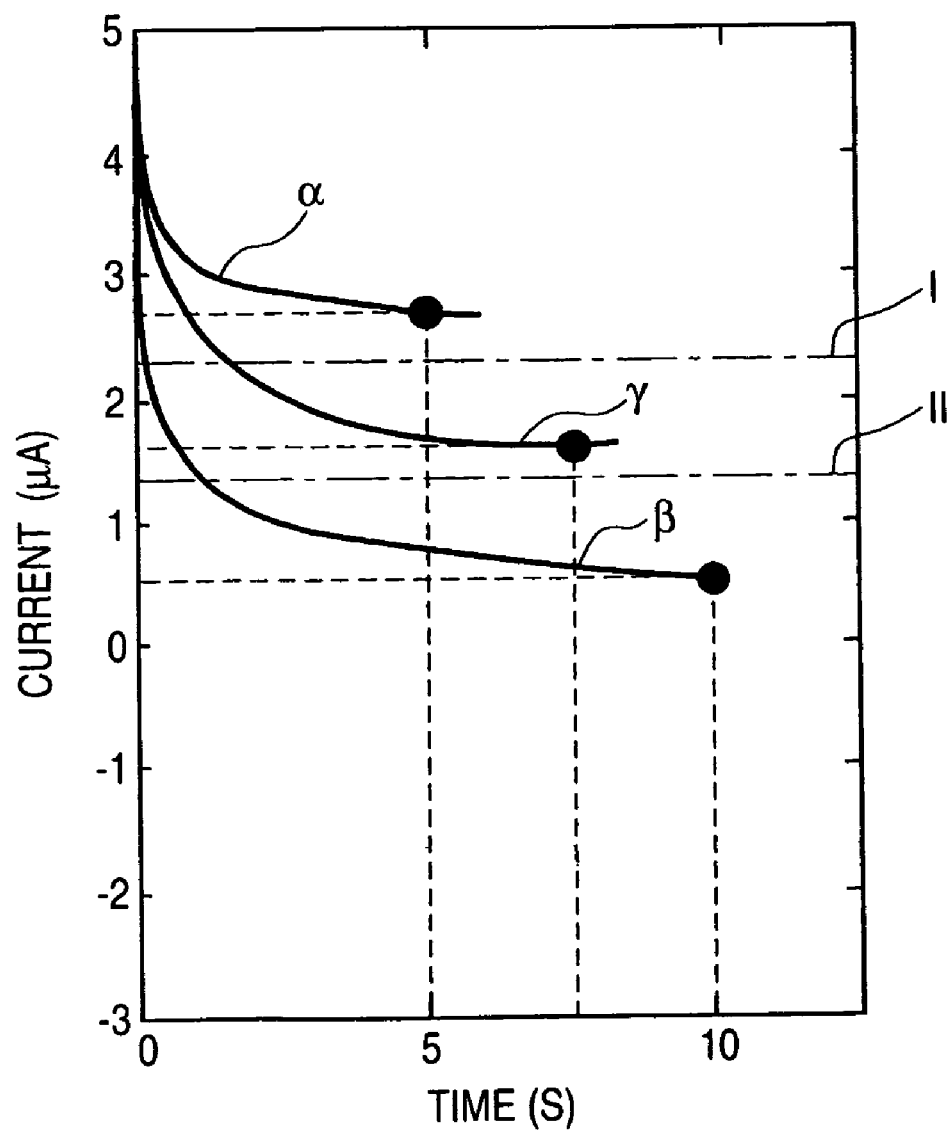
FIG. 7 is a diagram showing the elapsed time for currents measured by three biosensor chips.

Furthermore, in the description of the above described mode, only one current value has been set as a reference. However, a plurality of predesignated setup, current values may be employed to compute a blood sugar level. A mode for measuring a blood sugar level using two predesignated setup values will be explained based on FIG. 7. In FIG. 7, a current curve α, of a sample A for a first biosensor chip, a current curve β, of a sample B for a second biosensor chip, and a current curve γ, of a sample C for a third biosensor chip, are shown. The current curve α and the current curve β are the same as the current curves α and β shown in FIG. 6. As two predesignated current reference values, a first reference value I is set to 2.2 μA, and a second reference value II is set to 1.2 μA.

The current values of the individual samples A, B and C are measured. Since, after an elapse of five seconds, the current curve α exceeds the first reference value I of 2.2 μA, the measurement of the sample A is terminated, and the standard curve f1 in FIG. 5 is employed to compute the blood sugar level of the sample A. Since the current curves for the samples B and C are below the first reference value I, the measurement of the current is continued, and upon an elapse of 7.5 seconds, whether the second reference value II of 1.2 μA is exceeded is determined. As a result, it is determined that the current curve γ exceeds the second reference value and measurement of the sample C is terminated, and the standard curve C is selected in accordance with the determination based on the second reference value, i.e., the standard curve f3 shown in FIG. 5 is employed to compute the blood sugar level of the sample C. Since the second threshold value is not exceeded for the sample B, upon the elapse of ten seconds from the start of the measurement, the measurement is terminated, and the blood sugar level of the sample B can be computed based on the standard curve f2. As described above, when a plurality of different reference values (predesignated values) are set, and a plurality of different measurement periods are set, an accurate measurement can be conducted in a short period of time, in accordance with the concentration of the sample stored in the biosensor chip.

In the standard curve table in FIG. 5, the standard curves f1, f2 and f3 are two-dimensional linear lines having inherent, individual inclinations. However, in accordance with the biosensor chip to be used and other conditions, a standard curve table for curves, a standard curve table including both linear lines and curves, or a standard curve table of a polyline type, may be employed. When the type, for example, of the enzyme of a drug to be stored in the reaction space of a biosensor chip is varied, or when the size of a reaction space, a temperature, etc., differs, a difference occurs in data obtained through measurement (a current value, a charge value, etc.). Therefore, in accordance with the condition of a biosensor chip to be measured, only a standard curve table stored in the controller need be changed, for an accurate blood sugar level to be quickly measured. Further, calibration information may be stored in the controller, and in accordance with the condition of a biosensor chip or the characteristic of a measurement machine, a calibration factor may be employed when a blood sugar level is computed based on a standard curve. In this manner, a blood sugar level can more accurately be obtained.

The present invention has been explained in detail by referring to the specific modes. However, it will be apparent to one having ordinary skill in the art that the present invention can be variously modified or altered, without departing from the spirit and scope of the invention. The present invention is based on Japanese Patent Application No. 2005-267706, filed Sep. 14, 2005, and the contents of the application are included as references.

Figure 8:
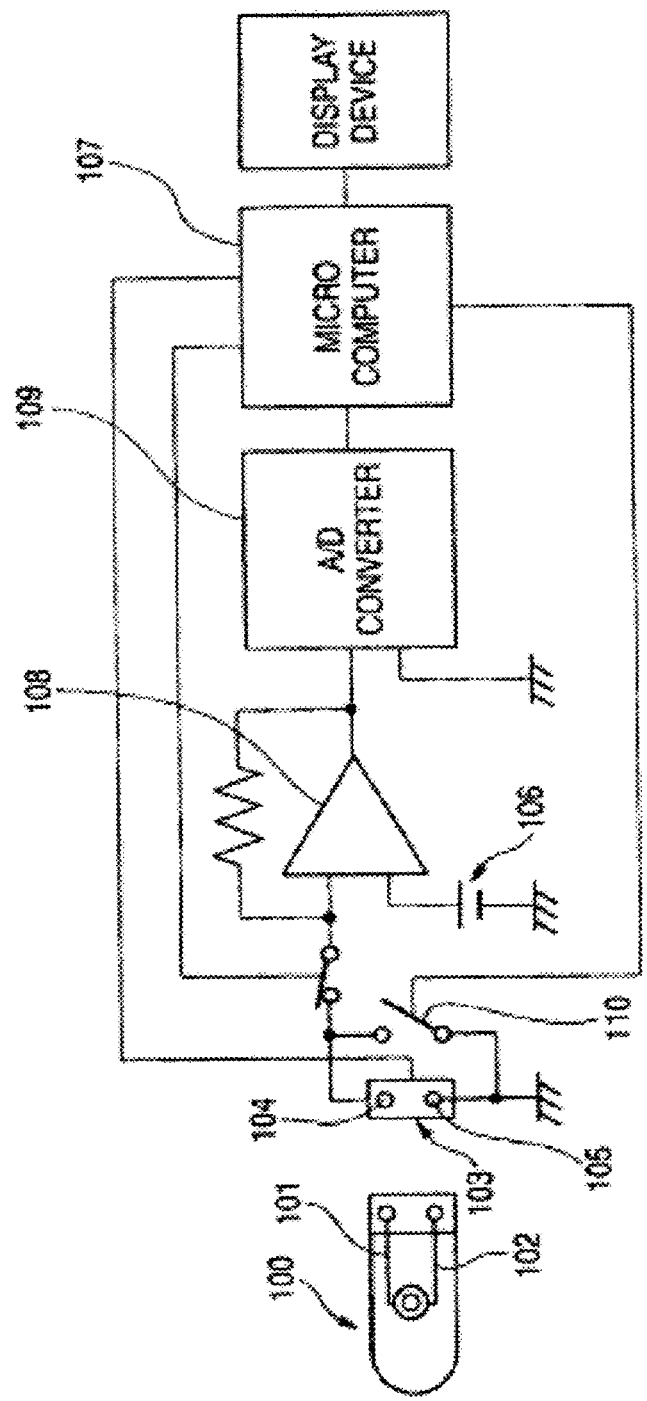
FIG. 8 is an explanatory diagram for explaining a conventional biosensor measurement method.
Figure 9:
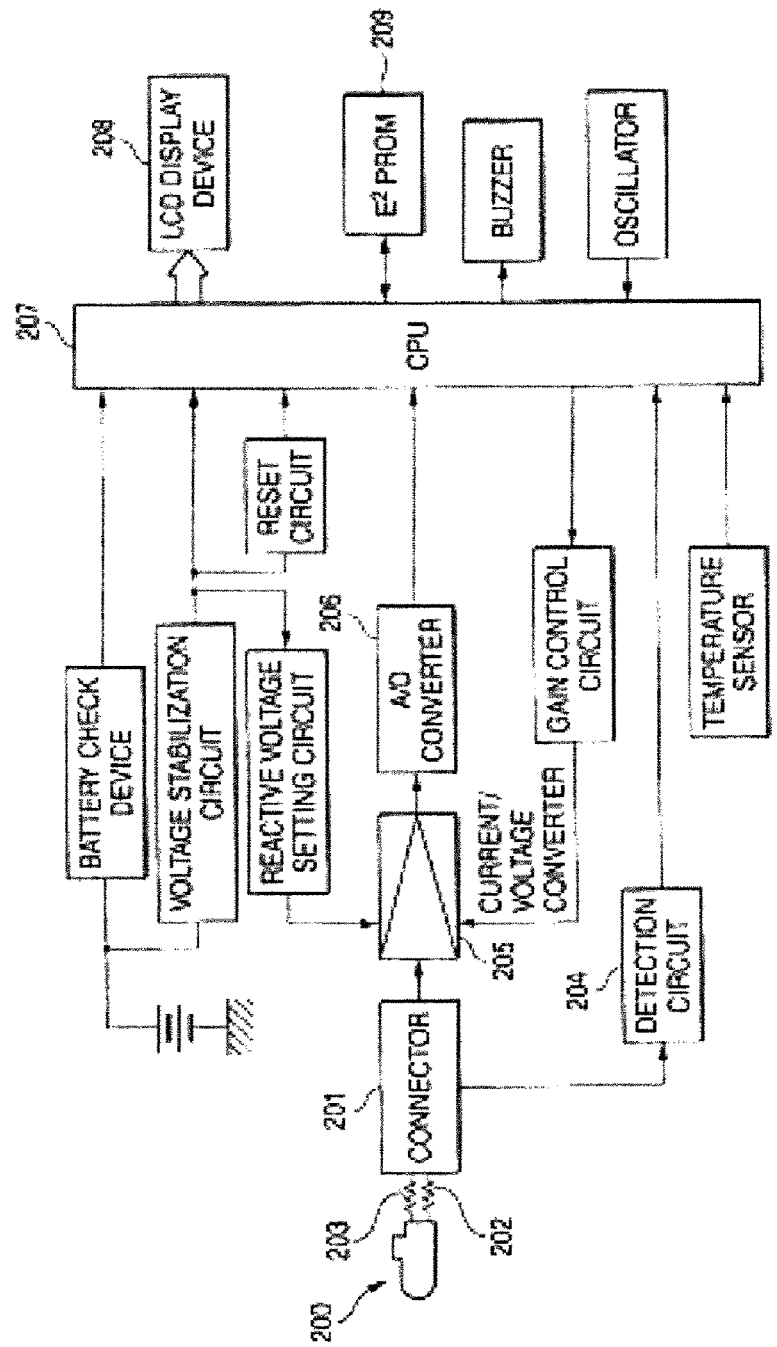
FIG. 9 is an explanatory diagram for explaining another example conventional biosensor measurement method.

[FIG. 2]
21: POWER SOURCE
24: CONTROLLER
25: DISPLAY
[FIG. 3]
STEP 1: CONNECT BIOSENSOR TO MEASUREMENT MACHINE.
STEP 2: INTRODUCE SAMPLE IN BIOSENSOR.
STEP 3: APPLY VOLTAGE TO BIOSENSOR.
STEP 4: MEASURE CURRENT VALUE UPON ELAPSE OF 5 SECONDS.
STEP 5: CURRENT VALUE SMALLER THAN 2 μA?
STEP 6: END MEASUREMENT.
STEP 7: EMPLOY STANDARD CURVE f1 TO COMPUTE BLOOD SUGAR LEVEL. END MEASUREMENT
STEP 8: CONTINUE MEASUREMENT
STEP 9: MEASURE CURRENT VALUE UPON ELAPSE OF 10 SECONDS.
STEP 10: EMPLOY STANDARD CURVE f2 TO COMPUTE BLOOD SUGAR LEVEL.
A1: END MEASUREMENT
[FIG. 4]
A1: CURRENT
A2: VOLTAGE
A3: TIME
[FIG. 5]
A1: GLUCOSE CONCENTRATION
A2: CURRENT
A3: BLOOD SUGAR LEVEL
[FIG. 8]
107: MICRO COMPUTER
109: A/D CONVERTER
A1: DISPLAY DEVICE
[FIG. 9]
201: CONNECTOR
204: DETECTION CIRCUIT
205: CURRENT/VOLTAGE CONVERTER
206: A/D CONVERTER
208: LCD DISPLAY DEVICE
A1: BATTERY CHECK DEVICE
A2: VOLTAGE STABILIZATION CIRCUIT
A3: REACTIVE VOLTAGE SETTING CIRCUIT
A4: RESET CIRCUIT
A5: GAIN CONTROL CIRCUIT
A6: TEMPERATURE SENSOR
A7: BUZZER
A8: OSCILLATOR

The invention claimed is:

1. A biosensor measurement machine comprising:
a voltage application unit for applying a voltage to a biosensor chip;
a measurement unit for measuring a current or a charge generated by the voltage application unit; and
a control unit for determining whether a measurement should be continued, based on a current value or a charge value measured by the measurement unit,
wherein the control unit is configured to:
compare the current value or the charge value with a reference value to determine whether the measurement should be continued,
terminate the measurement of the current value or the charge value either when it is determined that the current value or the charge value exceeds the reference value, or after a predetermined time has passed, whichever occurs first,
and,
perform a measurement of a chemical substance to determine the concentration of the chemical substance based on said current value or charge value measured immediately prior to termination of the measurement as measured by the measurement unit.

2. The biosensor measurement machine according to claim 1, wherein
a plurality of different values are prepared for use as reference values.

3. The biosensor measurement machine according to claim 1, wherein
the control unit also includes a plurality of different standard curve tables.

4. A biosensor measurement system comprising:
a biosensor measurement machine according to claim 1,
a biosensor chip; and
a connector connecting the biosensor measurement machine and a distal end of the biosensor chip.

5. The biosensor measurement system according to claim 4, wherein
a biosensor chip includes glucose oxidase as an enzyme, and has a cavity volume equal to or smaller than 300 nl (nanoliters).

6. A biosensor measurement method comprising the steps of:
applying a voltage to a biosensor chip;
measuring a current or a charge generated by application of the voltage;
determining whether a measurement should be continued, based on a current value or a measured charge value, by comparing the current value or the charge value with a reference value;
terminating the measurement of the current value or the charge value either after determining that the current value or the charge value exceeds the reference value, or after a predetermined time has passed, whichever occurs first;
and;
performing a measurement of a chemical substance to determine the concentration of the chemical substance based on said current value or said charge value measured immediately prior to termination of the measurement.

* * * * *